US012797557B2

(12) United States Patent
Morse

(10) Patent No.: US 12,797,557 B2

(45) Date of Patent: Nov. 17, 2026

(54) SYRINGE NEEDLE SAFETY SYSTEM

(71) Applicant: David Shannon Morse, Las Vegas, NV (US)

(72) Inventor: David Shannon Morse, Las Vegas, NV (US)

( * ) Notice: Subject to any disclaimer, the term of this patent is extended or adjusted under 35 U.S.C. 154(b) by 546 days.

(21) Appl. No.: 17/477,490

(22) Filed: Sep. 16, 2021

(65) Prior Publication Data

US 2022/0249784 A1 Aug. 11, 2022

Related U.S. Application Data

(60) Provisional application No. 63/148,566, filed on Feb. 11, 2021.

(51) Int. Cl.

*A61M 5/32* (2006.01)

*A61M 5/50* (2006.01)

(52) U.S. Cl.

CPC ........ *A61M 5/3271* (2013.01); *A61M 5/3204* (2013.01); *A61M 5/3216* (2013.01); *A61M 5/5086* (2013.01); *A61M 2005/3215* (2013.01); *A61M 2005/3247* (2013.01); *A61M 2005/3254* (2013.01); *A61M 2209/04* (2013.01)

(58) Field of Classification Search

CPC ........ A61M 5/3204; A61M 2005/3215; A61M 2209/04; A61M 2209/082; A61M 2209/086

See application file for complete search history.

(56) References Cited

U.S. PATENT DOCUMENTS

| | | | | |
|---|---|---|---|---|
| 4,894,055 A | | 1/1990 | Sudnak | |
| 4,955,865 A | * | 9/1990 | Steiner ................ | A61M 5/3205 604/263 |
| 4,979,945 A | * | 12/1990 | Wade .................. | A61M 5/3213 248/229.11 |
| 4,995,871 A | * | 2/1991 | Sasaki ................. | A61M 5/3205 220/348 |
| 5,067,949 A | * | 11/1991 | Freundlich .......... | A61M 5/3213 604/110 |
| 5,183,469 A | * | 2/1993 | Capaccio ............ | A61M 5/3213 206/365 |
| 5,242,426 A | * | 9/1993 | Pituch ................ | A61M 5/3213 29/281.1 |
| 5,292,313 A | * | 3/1994 | Fallas ................. | A61M 5/3213 604/263 |
| 5,308,582 A | * | 5/1994 | Serra ................... | A61M 5/3213 269/239 |

(Continued)

FOREIGN PATENT DOCUMENTS

WO WO-2017186695 A1 * 11/2017 ....... A61B 5/150022

*Primary Examiner* — Kami A Bosworth

(74) *Attorney, Agent, or Firm* — PatentPC PowerPatent; Bao Tran

(57) ABSTRACT

A housing or enclosure is provided with a notch or an opening to receive the tip of a syringe with a needle and cap assembly. A user inserts the syringe into the notch or opening and guides the needle and cap assembly into an assembly that allows easy separation of the needle and cap. After separation, the user can inject the needle into a patient as usual, and thereafter place the exposed needle back into the notch or opening. A cap placement assembly uses a manual lever or a motor to secure the cap in place the needle and release the syringe/needle if needed.

11 Claims, 6 Drawing Sheets

(56) References Cited

U.S. PATENT DOCUMENTS

| | | | | |
|---|---|---|---|---|
| 5,356,385 | A * | 10/1994 | Latini | A61M 5/3213 604/110 |
| 5,586,976 | A * | 12/1996 | Coutoumanos | A61M 5/3213 128/919 |
| 7,314,464 | B2 | 1/2008 | Giambattista | |
| 2006/0258991 | A1* | 11/2006 | Lin | A61M 5/3213 604/263 |
| 2008/0210890 | A1* | 9/2008 | Fago | G21F 5/018 250/506.1 |
| 2009/0014462 | A1* | 1/2009 | Costa | A61M 5/3205 221/185 |
| 2018/0280625 | A1* | 10/2018 | Cox | A61M 5/3204 |

* cited by examiner

SYRINGE NEEDLE SAFETY SYSTEM

This application claims priority to Provisional Ser. 63/148,566 filed Feb. 11, 2021, the content of which is incorporated by reference.

BACKGROUND

The present invention is a safety system for an injection device.

Used syringes with exposed needles present a substantial health hazard and can result in transmission of a number of potentially life-threatening diseases such as hepatitis, acquired immune deficiency syndrome (AIDS), and other various diseases. One group which is particularly at risk in dealing with such devices are professional health care workers who must handle these skin-puncturing contaminated devices after they have been used.

For example, during surgery, a scrub technician hands the surgeon a needle on a syringe to inject medication such as a local anesthetic. The technician then recaps the needle to protect him or her against accidental injury by the needle before placing it back on a surface like a Mayo stand in order to possibly be used again. However, the recapping process itself exposes the technician to a small risk of injury during the placement of the cover over the needle.

SUMMARY

In one aspect, a housing or enclosure is provided with a notch or an opening to receive the tip of a syringe with a needle and cap assembly. A user inserts the syringe into the notch or opening and guides the needle and cap assembly into an assembly that allows easy separation of the needle and cap. After separation, the user can inject the needle into a patient as usual, and thereafter place the exposed needle back into the notch or opening. A cap placement assembly uses a manual lever or a motor to secure the cap in place the needle and release the syringe/needle if needed.

In another aspect, a method to safely handle a syringe with a needle and a needle cap includes: providing a housing or enclosure is provided with a notch or an opening to receive the tip of a syringe with a needle and cap assembly; inserting the syringe into the notch or opening and guiding the needle and cap assembly into a latch assembly that secures the cap and allows separation of the needle and cap; removing the syringe from the housing and exposing the needle for use; after injection, placing the exposed needle back through the notch or opening and securing the cap on the exposed needle; and releasing hold on the cap to allow removal of the syringe with the cap on the needle.

In implementations of the above aspects, the notch is V-shaped. The cap handling assembly can be motorized. In an manual version, a lever having a first position to secure the cap to the housing and a second position to disengage the cap. An adhesive on the housing to secure the device to a surface. A screw and a corresponding mount can be provided to removably secure the housing to a mount surface. The device can be placed into autoclave for cleaning. The device can also be disposable.

Advantages of the system may include one or more of the following. The system protects patients and healthcare personnel from accidental skin puncture injuries from contaminated needles. The system also provides a safe and efficient means for disposing the same. The present needle guard assembly overcomes many of the limitations and shortcomings associated with known needle shielding devices and teaches the construction and operation of a relatively simple needle guard device which effectively protects health care workers and others from accidental injuries by contaminated needle pricks. The present assembly includes a base member, a telescoping slidably movable guard member, spring means for normally biasing the guard member to its fully extended position completely surrounding the needle, and a novel locking mechanism for preventing subsequent use of the device as will be hereinafter explained. The base member is generally tubular in shape having one end portion open so as to telescopingly receive the guard member which is positioned therewithin. The opposite end portion of the base member includes a syringe port formed by flanged wall means, the syringe port being sized and dimensioned so as to snugly fit onto the barrel portion of a conventional needle cap. The syringe port remains engaged with the syringe by means of friction, although adhesive means may likewise be applied to the interior wall surfaces of the syringe port to provide additional strength and stability to the joinder. Also, the syringe port can be fashioned and dimensioned to accommodate all known syringe sizes as well as other needle-bearing devices.

These and other objects and advantages of the present invention will become apparent to those skilled in the art after considering the following detailed specification which discloses several different embodiments of the present device in conjunction with the accompanying drawings.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which.

DESCRIPTION

As used herein, the term injection device refers to any device which may contain a medicament, in whatever form (e.g., liquid, solid, powder, or combinations thereof), and which may be used to inject such medicament into a patient. As used herein, the term injection device includes sterilized and non-sterilized devices, filled (with medicament) and unfilled devices, and any variation or combination thereof. For example, an injection device may be a pen-type injector which receives a syringe or cartridge, and on which the inventive needle assembly may be provided.

FIGS. 1A-1D show an exemplary housing that can be secured to a stand such as a Mayo stand. The Mayo stand is a removable instrument tray set on a movable stand that is positioned over or adjacent to a surgical site; it provides a place for sterile instruments and supplies used during surgery. The scrub technician picks up a Mayo stand cover to drape the Mayo stand. The scrub then steadies the stand with one of his/her feet and places the drape over the nearest end of the stand. The cover is then pulled over the stand and the housing is then secured to the cover/stand. In one embodiment, the housing can be secured to the stand using one or more clamps that allows secure insertion of a needle portion of the syringe to the housing.

The syringe has a needle and a detachable needle cap to protect the syringe needle and to keep the needle aseptic. The detachable cap provides mechanical protection and be convenient to remove pin cover before plunging the needle into the patient. The device 10 provides this protection for the medical professionals without exposing them to accidental pricks from the needle.

Figure 1A:
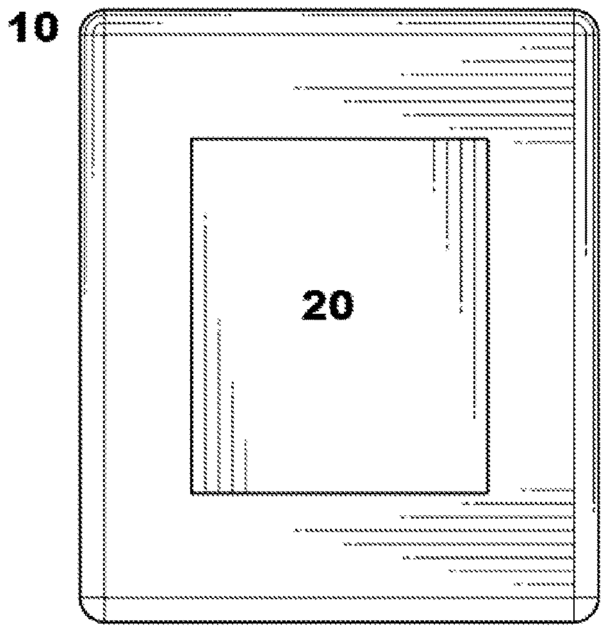
FIGS. 1A-1D shows an exemplary safety system for handling syringe with a needle.
Figure 1B:
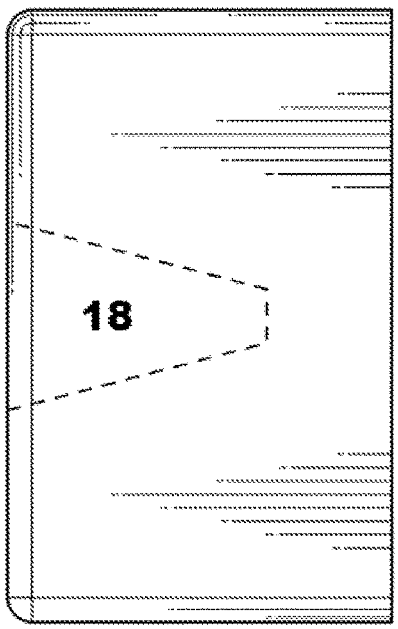
Figure 1C:
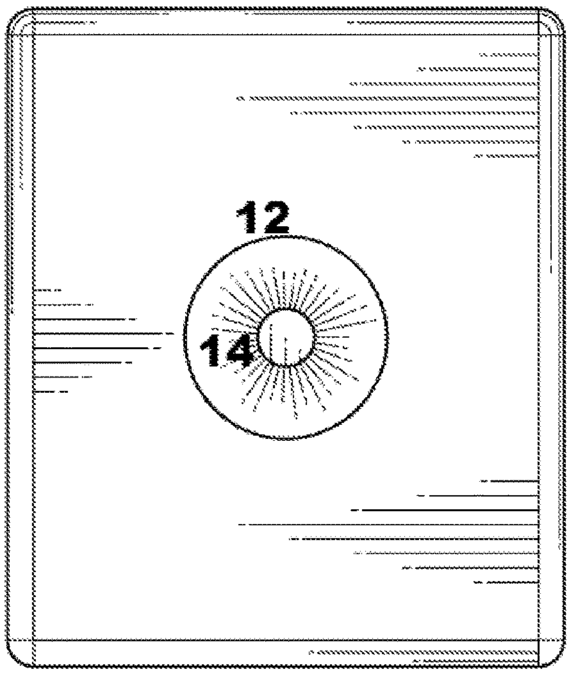
Figure 1D:
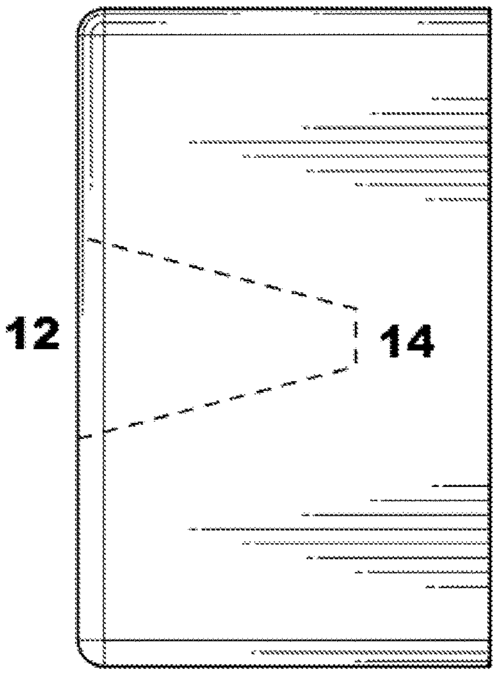
Figure 2A:
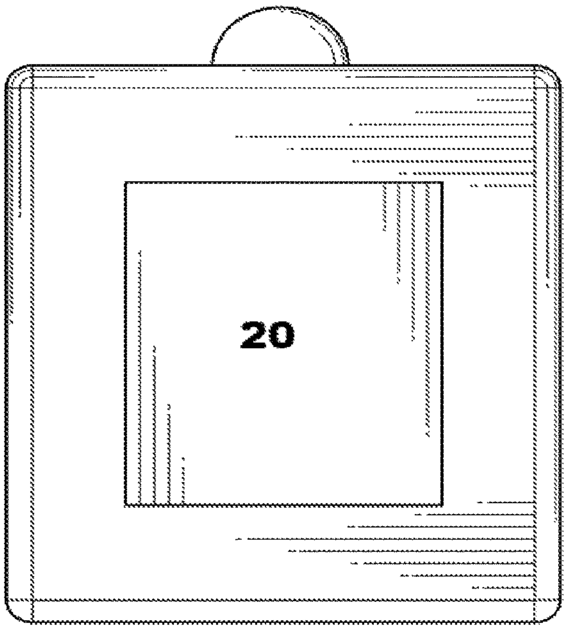
FIGS. 2A-2D shows another exemplary needle cover removal system.
Figure 2B:
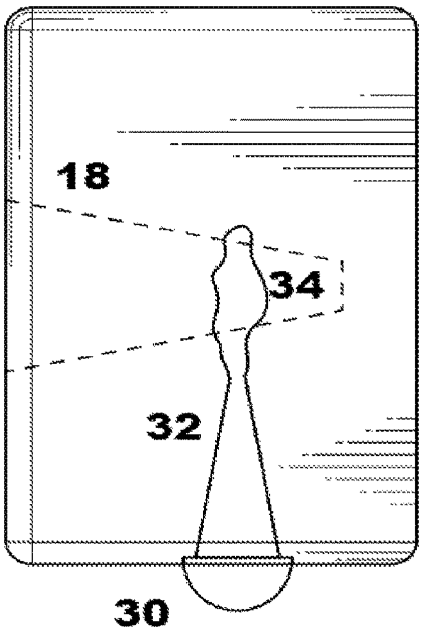
Figure 2C:
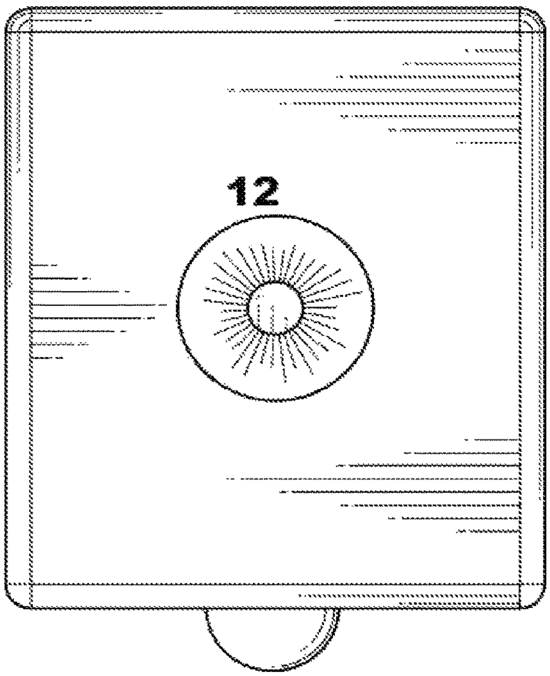
Figure 2D:
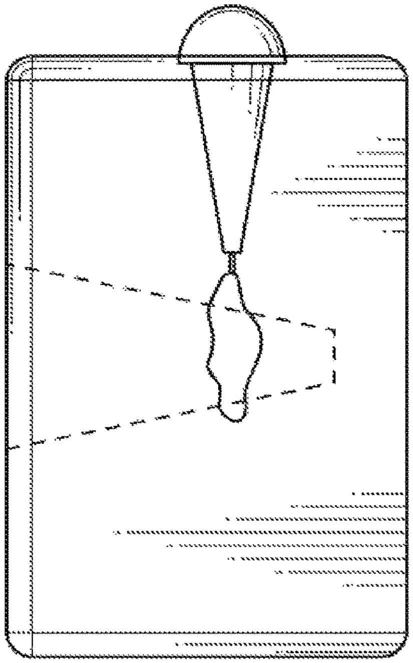

As shown in FIG. 1A, the device 10 has an adhesive back 20 on one side that secures the device to the stand. On the other side is an opening 12 that receives the syringe assembly with the needle and cap through a device cavity 18 that is V-shaped. The needle cap is gripped and held by end portion 14 to allow the syringe needle to be exposed and ready for injection. After injection, the syringe can be reinserted through the opening 12 into the cap held by opening 14. After the cap is on the needle, the capped syringe can be safely removed from the device 10.

In one embodiment, the device 10 has a V-shaped cone or notch 18 on top where the technician would slide the needle into the V-shape cone and lock the syringe in place. A lever on a side of the housing is moved to release the hold on the cover. The user can place the needle back into the cover, with the hand behind the needle to provide a safe environment.

FIG. 2 shows an exemplary needle cover removal system. When the needle is pushed into the cone with the V-shape, the cap is locked in place. To release the syringe, the user pulls down a lever 30 and then pop-out the needle cap. The lever 30 has a body 32 that extends from the exterior of device 10 into the notch 18 with a release end 34.

Figure 3A:
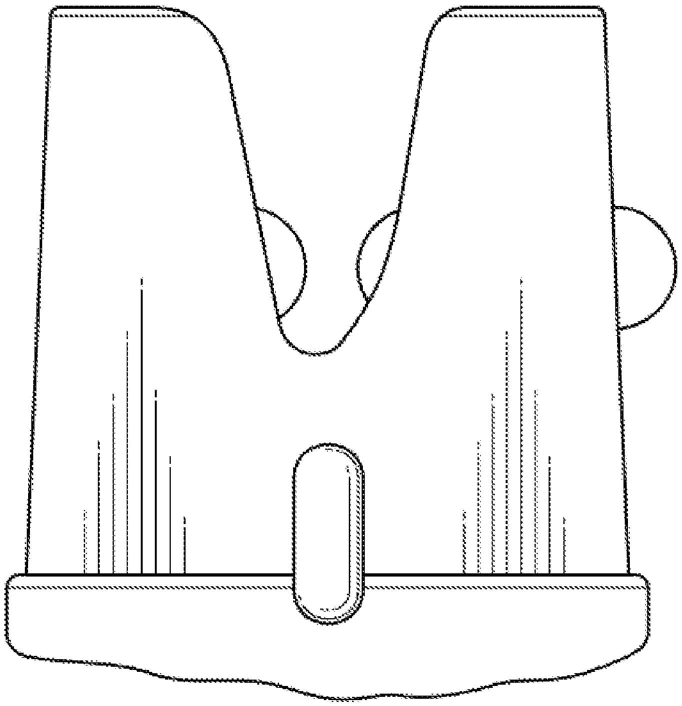
FIGS. 3A-3B show another embodiment of the safety system for handling syringe with a needle.
Figure 3B:
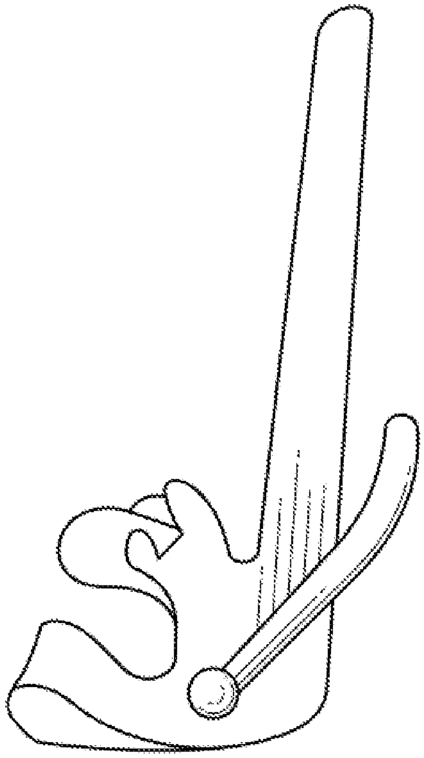
Figure 4A:
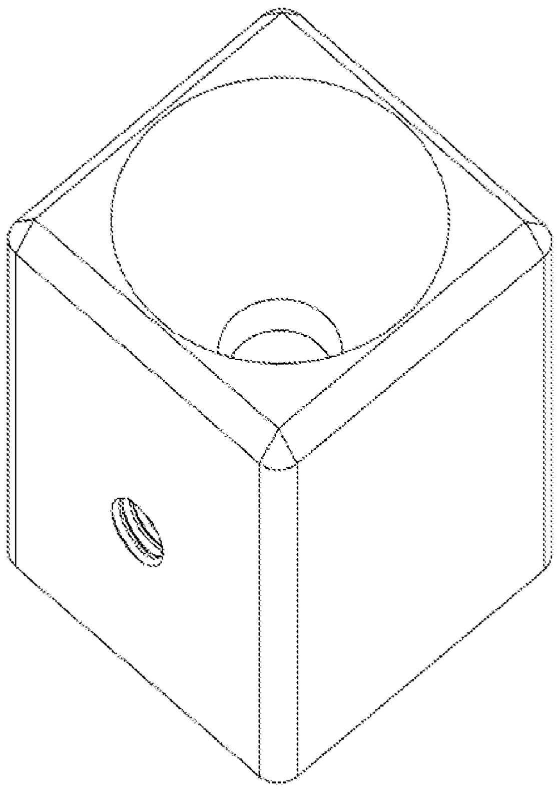
FIGS. 4A-4E show a screw cap holding embodiment of the syringe safety system.
Figure 4B:
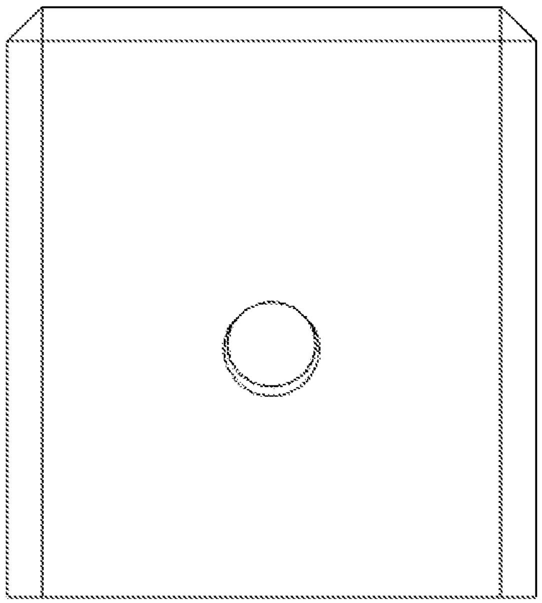
Figure 4C:
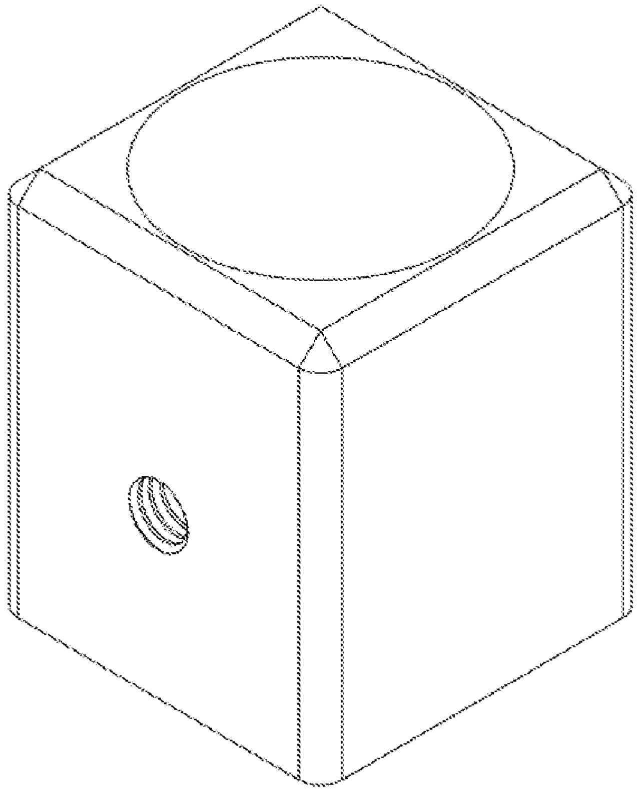
Figure 4D:
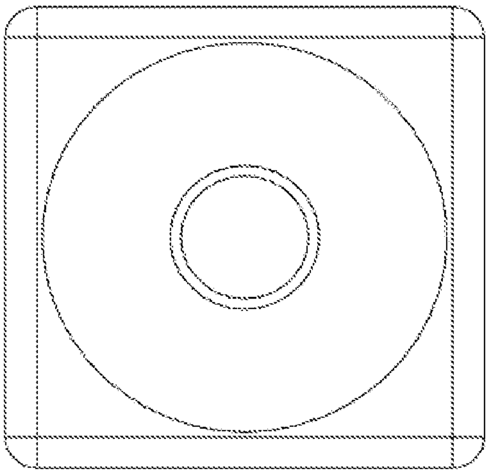
Figure 4E:
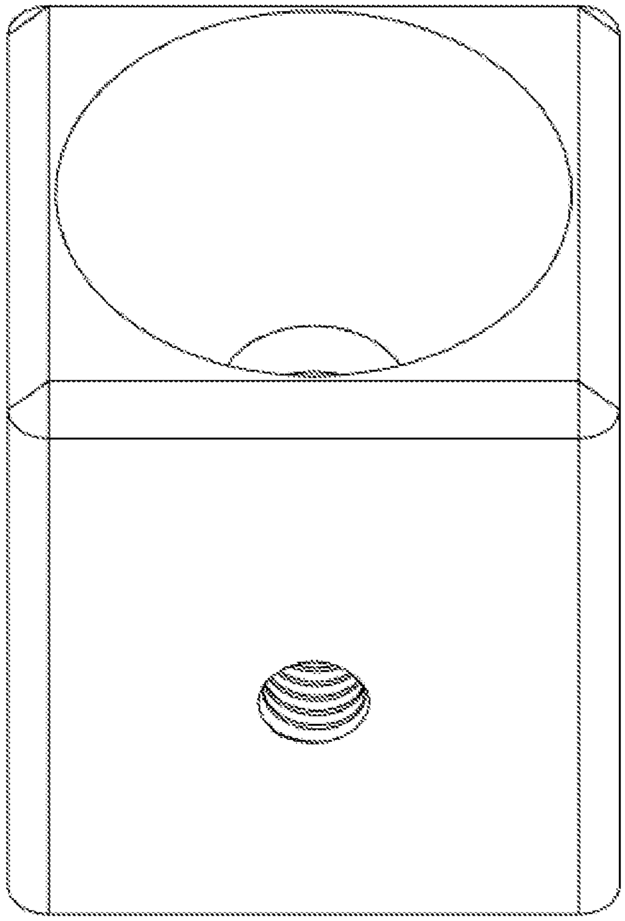

FIG. 3A-3B show in more details the lever or latch 30 that allows the needle cap to be held in place to expose the needle, and then to subsequently release the cap, when the needle has been reinserted into the cap. The lever allows the user to manually remove the grip holding the cap inside the device 10 until after injection when the needle is reinserted onto the cap for user protection and then the needle and cap combination can be released for free movement. In one operation, the syringe/needle is inserted into a V notch with small tabs or protrusions embedded in the V-notch. The syringe/needle combination is placed so that the notches are between the syringe and cap. When pulled back from the housing, the cap would be separated from the syringe, exposing the needle for injection. When the injection is done, the user can push the syringe with the exposed needle back into the V-shaped notch, and the cap can be placed on a moveable assembly that is motorized to enclose the needle with the cap to avoid unnecessary exposure of the user to the exposed needle. In this manner, the lever can be provided for the user to manually move the cap over the needle.

FIGS. 4A-4E show a screw cap holding embodiment of the syringe safety system. This embodiment provides a screw receiving cavity to access the cap, wherein the screw has a first position to secure the cap to the housing and a second position to disengage the cap. A user rotates a screw in one direction to secure the cap to the housing and rotates the screw in a counter-direction to release the cap. In one embodiment, the housing is disposable and the screw can be autoclaved for reuse. In another embodiment where the housing and the a recyclable finger moveable screw cap end can be placed in the autoclave for disinfection and reuse.

Other embodiments of the present device include various configurations associated with the lever, latch or locking mechanism and the positioning of the latching members associated therewith. For example, one embodiment of the present device includes locating the resilient latching members on the guard member of the present assembly, while still another embodiment includes locating the latching members on the flanged wall means associated with the syringe port. Regardless of where the resilient latching members are positioned, the several embodiments of the present invention operate substantially similarly as will be hereinafter explained.

The system provides safe and reliable means for protecting health care workers and others from accidentally sticking themselves with used needles. The housing with the needle guard assembly is fabricated to easily attach to any conventional syringe or other needle-bearing device. In another embodiment, the easy to use needle guard assembly automatically encases the needle after use. The housing does not interfere with the operation of the syringe or other needle-bearing device. The housing with the needle guard assembly is structurally and operationally relatively simple and inexpensive to make, and further is easy to install and use.

Although it is recognized that various acceptable materials of construction are available and could equally be employed to fabricate the various components associated with the several embodiments of the present needle guard assembly disclosed herein, it is usually preferred that the present devices be made of a strong plastic material in a sterile, single use pack. A version that is reusable and able to be processed along with the surgical instruments is also described.

While the foregoing describes syringe-based medicament delivery systems—the specific medicament delivery device not limiting the scope of spirit of the present invention. The safety shield system of the present invention is preferably, but not exclusively, adapted for use with syringes, but can also be used with pen injectors. Such pen injectors generally include a tubular body portion adapted to receive a conventional vial for dispensing a liquid medicament. The pen injector has an end configured to receive a pen needle such as, for example, the needle assembly of the present invention. Typically, the pen injector has an external thread to receive a complementarily configured thread on the needle assembly. Once the needle assembly is secured to the pen injector, the first end of the needle cannula pierces the rubber septum of the vial carried by the pen injector. Typical pen injectors may be single-dose, in which the entire contents of medicament within the vial are dispensed in a single injection, or multi-dose, in which only part of the contents of medicament within the vial are dispensed in an injection. For the latter case, the pen injector may include dose setting features.

The entire contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and may be used in conjunction with or substituted for components and methods described elsewhere in the disclosure within the scope of the invention.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose.

Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

What is claimed is:

1. A method to safely handle a syringe with a needle cap assembly, comprising:

providing a housing or an enclosure with a notch or an opening to receive the needle cap assembly, wherein the notch or the opening includes one or more tabs or protrusions embedded therein;

inserting the needle cap assembly into the notch or the opening and guiding the needle cap assembly into a latch assembly that secures a cap of the needle cap assembly with a lever extending through a tapered wall forming the notch or the opening;

releasing the cap from a needle of the needle cap assembly and allowing separation of the syringe with the needle from the cap;

exposing the needle for use;

after injection, placing the syringe with the exposed needle back through the notch or the opening into the cap and securing the needle within the cap to protect a user from an accidental needle stick.

2. The method of claim 1, wherein the notch or the opening is V-shaped.

3. The method of claim 1, comprising releasing the lever to allow removal of the needle cap assembly from the housing or the enclosure.

4. The method of claim 1, wherein the lever has a first position to secure the cap to the housing or the enclosure and a second position to disengage the cap.

5. The method of claim 1, comprising providing an adhesive on the housing or the enclosure to secure the housing or the enclosure to a surface.

6. The method of claim 1, comprising placing the housing or the enclosure into an autoclave for cleaning.

7. The method of claim 1, wherein the housing or the enclosure is disposable.

8. A method, comprising:

providing a housing or an enclosure with a notch or an opening to receive a tip of a syringe with a needle-and-cap assembly and providing the housing or the enclosure with a latch assembly coupled to a lever extending through a tapered wall forming the notch or the opening and that secures a cap of the needle-and-cap assembly and allows separation of a needle of the needle-and-cap assembly from the cap, wherein the notch or the opening includes small tabs or protrusions embedded therein;

inserting the needle-and-cap assembly into the notch or the opening;

pulling the syringe with the needle attached thereto from the housing or the enclosure such that the cap remains contained in the housing or the enclosure and exposing the needle of the needle-and-cap assembly for use;

after injection, placing the syringe with the exposed needle through the notch or the opening and securing the needle inside the cap to protect a user from an accidental needle stick, and releasing the cap to allow removal of the syringe with the cap on the needle.

9. The method of claim 8, wherein the notch or the opening is V-shaped.

10. The method of claim 8, wherein the cap is released by disengaging the lever from the cap.

11. The method of claim 8, wherein the cap is released by moving the lever from a first position that secures the cap to the housing or the enclosure to a second position that disengages the cap.

* * * * *